United States Patent
Heismann et al.

(10) Patent No.: US 7,945,018 B2
(45) Date of Patent: May 17, 2011

(54) METHOD FOR PRODUCING PROJECTIVE AND TOMOGRAPHIC IMAGES USING AN X-RAY SYSTEM

(75) Inventors: Björn Heismann, Erlangen (DE); Eckhard Hempel, Fürth (DE); Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 346 days.

(21) Appl. No.: 12/223,061

(22) PCT Filed: Jan. 30, 2007

(86) PCT No.: PCT/DE2007/000160
§ 371 (c)(1),
(2), (4) Date: Jul. 22, 2008

(87) PCT Pub. No.: WO2007/087789
PCT Pub. Date: Aug. 9, 2007

(65) Prior Publication Data
US 2010/0220834 A1    Sep. 2, 2010

(30) Foreign Application Priority Data
Feb. 1, 2006 (DE) .......................... 10 2006 004 976

(51) Int. Cl.
*G01N 23/04* (2006.01)
(52) U.S. Cl. .......................................... 378/62; 378/145
(58) Field of Classification Search ............... 378/62, 378/145
See application file for complete search history.

(56) References Cited

U.S. PATENT DOCUMENTS

| | | | |
|---|---|---|---|
| 5,812,629 A | | 9/1998 | Clauser |
| 6,018,564 A | * | 1/2000 | Wilkins ........................... 378/62 |
| 2005/0286680 A1 | | 12/2005 | Momose |
| 2007/0183562 A1 | * | 8/2007 | Popescu et al. ................. 378/19 |
| 2007/0183583 A1 | * | 8/2007 | Baumann et al. ............. 378/145 |
| 2007/0183584 A1 | * | 8/2007 | Baumann et al. ............. 378/145 |

FOREIGN PATENT DOCUMENTS

| | | |
|---|---|---|
| EP | 1447046 A1 | 8/2004 |
| EP | 1731099 A1 | 12/2006 |

OTHER PUBLICATIONS

Jiang et al., X-ray Phase-Contrast Imaging with Three 2D Gratings, International Journal of Biomedical Imaging, vol. 2008, Article ID 827152, 2008, 8 pages.*
Wu et al., X-Ray cone-beam phase tomography formulas based on phase-attenuation duality, Optics Express, vol. 13, No. 16, Aug. 2005, pp. 6000-6014.*

(Continued)

*Primary Examiner* — Edward J Glick
*Assistant Examiner* — Alexander H Taningco
(74) *Attorney, Agent, or Firm* — Harness, Dickey & Pierce, P.L.C.

(57) ABSTRACT

An embodiment of the present invention discloses a method for producing projective and tomographic images using X-rays, allowing structures of similar composition to be imaged particularly well by combined evaluation of the behaviour of the test object with respect to the phase displacement during passage of the X-rays and its absorption. At least one embodiment of the invention also relates to an X-ray system and a CT system with respective source grids, phase grids, and analytical grids for carrying out the method.

30 Claims, 4 Drawing Sheets

OTHER PUBLICATIONS

Champenois et al., Fringe contrast in three grating Mach-Zehnder atomic interferometers, European Physical Journal D, 1999, pp. 363-374.*

Pfeiffer et al., Phase retrieval and differential phase-contrast imaging with low-brilliance X-ray sources, Nature physics Advance online publication, Mar. 2006, pp. 1-4.*

Weitkamp, Timm et al., Hard X-ray phase imaging and tomography with a grating interferometer, 2004, pp. 137-142.

Weitkamp, Timm et al.; X-ray phase imaging with a grating interferometer; Optics Express, vol. 13, No. 16, published Aug. 8, 2005, pp. 6296-6304; Optical Society of America; 13; Magazine; 2005.

Momose. A.; X-ray Talbot Interferometry for Medical Phase Imaging; AIP Conference Proceedings, vol. 716, S. 156-159; Others; 2004.

* cited by examiner

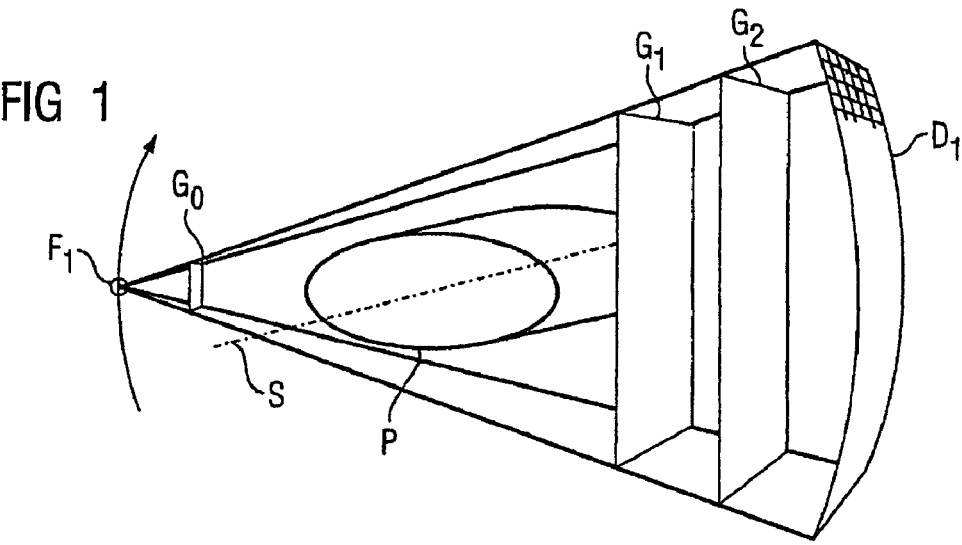
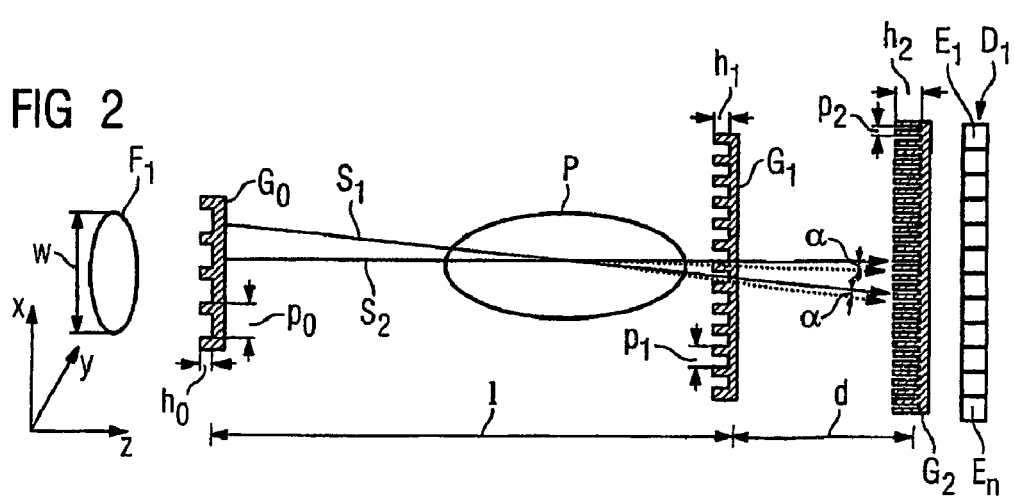

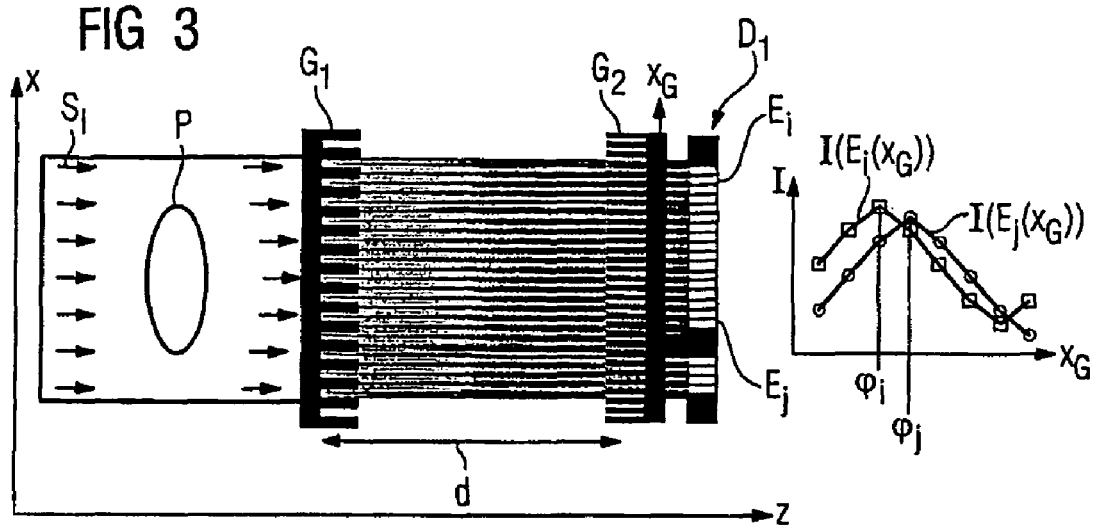
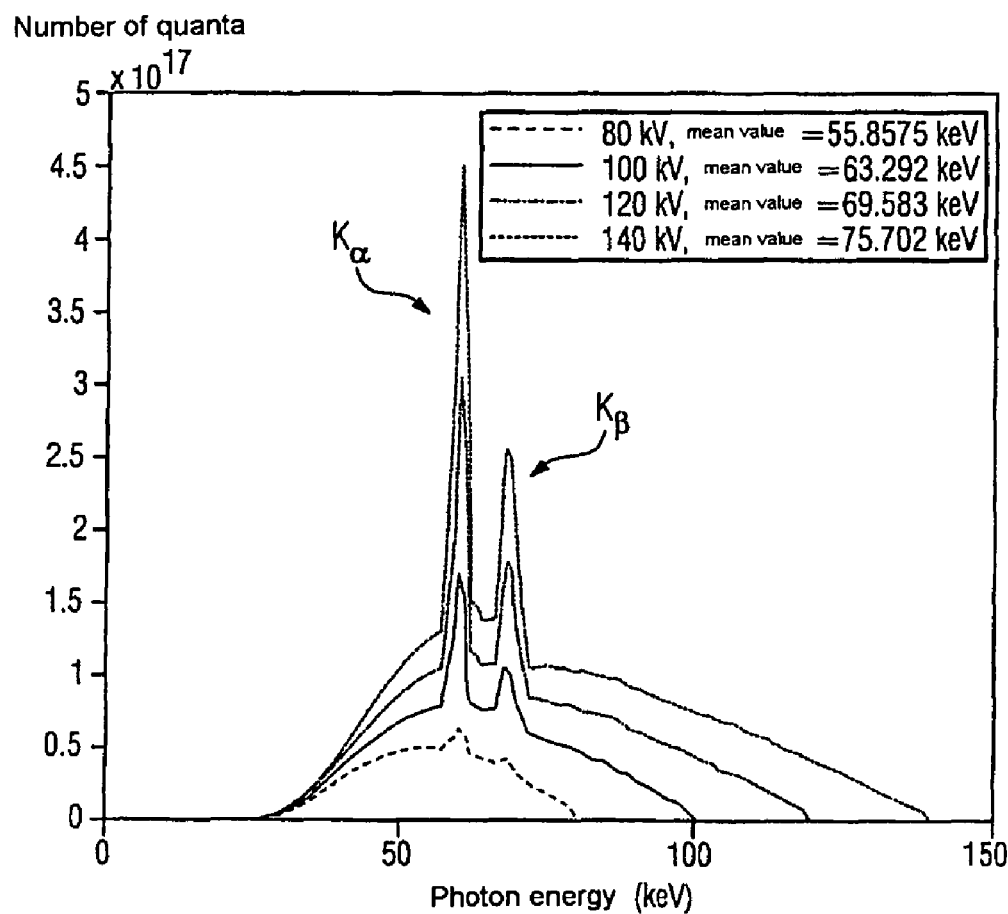

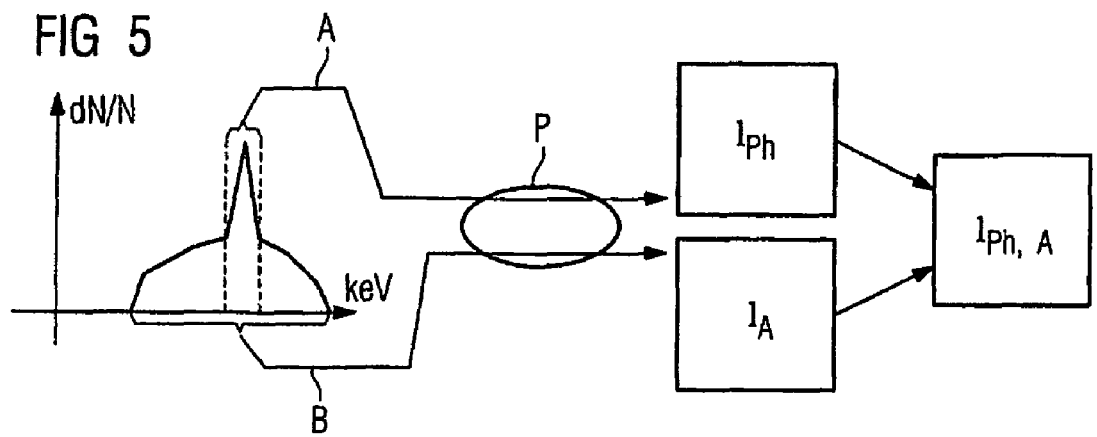
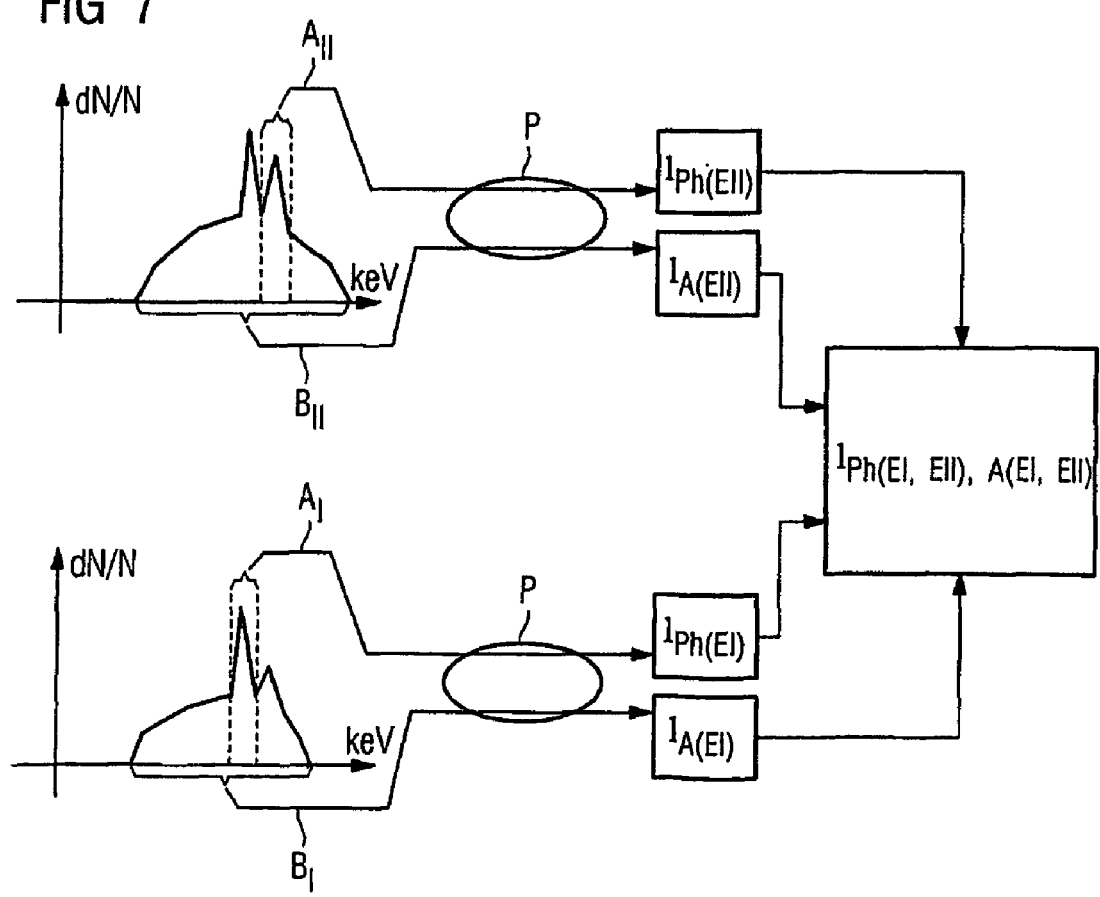

METHOD FOR PRODUCING PROJECTIVE AND TOMOGRAPHIC IMAGES USING AN X-RAY SYSTEM

PRIORITY STATEMENT

This application is the national phase under 35 U.S.C. §371 of PCT International Application No. PCT/DE2007/000160 which has an International filing date of Jan. 30, 2007, which designated the United States of America, and which claims priority on German patent publication DE 10 2006 004 976.4, filed Feb. 1, 2006, the entire contents of which are hereby incorporated herein by reference.

FIELD

At least one embodiment of the invention generally relates to a method for producing projective and tomographic images of an examination object, preferably a patient, having an X-ray system. In at least one embodiment, the examination object is scanned statically or circularly or spirally in rotary fashion with the aid of an X-ray tube having a focus, and the received radiation intensity is measured with the aid of a detector after passage through the examination object. Use may be made here of a set of X-ray optical gratings by which the phase shift of the X-radiation can be determined upon passage through the examination object.

BACKGROUND

In general computed tomography, tomographic images of an examination object, in particular of a patient, are taken with the aid of absorption measurements of X-rays that penetrate the examination object, a radiation source generally being moved circularly or spirally about the examination object, and a detector, for the most part a multirow detector with a multiplicity of detector elements, measuring the absorption of the radiation upon passage through the examination object on the side opposite the radiation source. For the purpose of tomographic imaging, tomographic slice images or volume data are reconstructed from the measured absorption data of all the measured spatial rays. Very fine absorption differences in objects can be displayed with the aid of these computed tomography images, but zones of similar chemical composition that naturally also have a similar absorption behavior are displayed only with unsatisfactory detail.

It is known, furthermore, that the effect of the phase shift upon passage of a ray through an examination object is substantially stronger than the absorption effect of the material penetrated by the radiation. Such phase shifts are known to be measured by the use of two interferometric gratings. These interferometric measuring methods are referred to, for example, in "X-ray phase imaging with a grating interferometer, T. Weitkamp et al., Aug. 8, 2005/Vol. 12, No. 16/OPTICS EXPRESS". In the case of this method, an examination object is trans-irradiated by a coherent X-radiation and subsequently guided through a pair of gratings, and the radiation intensity is measured directly after the second grating.

The first grating produces an interference pattern that images a Moiré pattern onto the detector lying therebehind with the aid of the second grating. If the second grating is slightly displaced, this likewise results in a displacement of the Moiré pattern, that is to say a change in the spatial intensity in the detector lying therebehind, which can be determined relative to the displacement of the second grating. If the change in intensity is plotted for each detector element of this grating, that is to say for each ray, as a function of the displacement path of the second grating, the phase shift of the respective ray can be determined. The fact that this method requires a very small radiation source is a problem, and therefore cannot be applied in practising computed tomography of relatively large objects, since formation of the interference pattern requires a coherent radiation.

The method shown in the abovenamed document requires a radiation source with an extremely small focus such that a sufficient degree of spatial coherence is present in the radiation used. However, when such a small focus is used there is then, in turn, an insufficient dose rate for examining a relatively large object. However, there is also the possibility of using a monochromatically coherent radiation, for example a synchrotron radiation, as radiation source, but the construction of the CT system is thereby rendered very expensive and so a widespread application is impossible.

This problem can be circumvented by arranging a first absorption grating inside the focus/detector combination in the beam path, directly following the focus. The alignment of the grating lines is in this case parallel to the grating lines of the interference grating following the examination object.

The slits of the first grating produce a field of individually coherent rays that suffices for producing the interference pattern known per se with the aid of the phase grating arranged downstream of the object in the ray direction.

It is possible in this way to use radiation sources that have dimensions corresponding to the normal X-ray tubes in CT systems or transmitted light X-ray systems, although the image resolution continues to be determined by the extent of the focus.

SUMMARY

At least one embodiment of the invention specifies a method for graphically displaying an object scanned by way of X-rays, which method displays in an improved way and with greater differentiation object regions with similar absorption, but at the same time also sufficiently differentiates differently absorbing regions. This method is intended to be capable of use both for tomographic and for projective images. A corresponding CT system and a corresponding X-ray system are also to be specified.

The inventors have realized, in at least one embodiment, that it can be particularly advantageous to combine the properties of X-ray phase contrast images and X-ray absorption images, this being applicable with reference both to tomographic images and to projective or transmitted light images. The absorption images can be used with particular advantage to display bone structures or the interfaces between bones and tissue, while it is possible additionally to use contrast agents and, if appropriate, previous segmentation also to obtain a vessel display with the aid of absorption images in a very accurate and richly detailed fashion. On the other hand, with such absorption images the structure of soft parts is scarcely discernible, and so this type of imaging is relatively unsuitable for displaying soft-part tissues or cartilage and sinew components. The phase contrast method is particularly suitable for this, since minimal changes already occur in the tissue composition in relation to relatively strong alterations upon passage of X-rays. It will therefore be particularly easy to detect structures in soft parts with the aid of phase contrast images.

However, it is disadvantageous of these images that the transitions between, for example, bones and soft parts come out relatively poorly. According to at least one embodiment of the invention, the advantages of both types of imaging are now combined with one another by virtue of the fact that appropriate superpositions of the two types of display are produced such that the richness of detail in the different types of imaging is stressed in each case. It can be particularly advantageous to this end when image processing is additionally performed either before the two images are merged or subsequently, such that, as the case may be, mutually disruptive influences are remote, a particularly viable weighting is selected, or, if appropriate, segmentations are carried out in advance. Such superposed images can either be produced only in black and white, or it is possible firstly to color the respective types of image and to display the pixels of the superposed images by way of appropriate mixed colors of the two types of image.

On the basis of the above-named considerations, the inventors, in at least one embodiment, propose in the field of computed tomography a method for producing tomographic images of an examination object, preferably a patient, having an X-ray CT system, at least the following method steps being carried out:

the examination object is scanned circularly or spirally with the aid of at least one X-ray tube having a focus, the received radiation intensity is measured with the aid of at least one detector, there being arranged between the at least one X-ray tube and the at least one detector a set of X-ray optical gratings that are trans-irradiated by the X-radiation and enable a phase contrast measurement, and a first grating being arranged between the focus and an examination object, and two gratings being arranged between the examination object and detector, for each ray lying in space between the focus and detector and that penetrates the examination object, at least three intensity measurements are determined with the aid of detector-side gratings respectively arranged offset from one another for the phase shift from this ray upon passage through the object, tomographic phase contrast images are reconstructed from the measured phase shifts of the rays, the absorption of each ray is determined upon passage through the examination object, tomographic absorption images are reconstructed from the absorption measurements, and subsequently, the tomographic absorption images and the tomographic phase contrast images are superposed and displayed.

As already mentioned above, it is particularly advantageous when the tomographic phase contrast images and/or the absorption images are subjected to image processing before superposition. It is thereby possible, for example, to carry out segmentations, to emphasize contrasts more effectively, or else to select a multicolor display or similar variants of the image processing.

During the subsequent superposition, the latter can be carried out either with equal weighting or different weighting, it being possible for this weighting to be set, for example, by the viewer individually, depending on subjective feeling. Alternatively, there is also the possibility that the images are weighted differently locally, it appearing to be sensible if in this case specific criteria referring to the image quality or image properties are used as a basis for the different weighting of the two images.

In accordance with the different type of configuration of the computed tomography system used, with the aid of which the phase contrast images and absorption images are carried out, it is also possible to select different variants for producing the phase contrast and absorption images. For example, the images can be produced with the aid of a simple computed tomography system having a single focus/detector system, the set of gratings being permanently integrated in the focus/detector system. It is thereby possible, on the one hand, to perform the phase shift per spatial ray between focus and detector by a number of measurements with a simultaneously displaced analysis grating (last grating upstream of the detector), the measurement of the absorption of the ray subsequently being carried out by summing up or by forming the average of all the measured values of this ray with the aid of a differently displaced grating.

Another possibility resides in that a computed tomography system is used which has at least two focus/detector systems, in which case a first focus/detector system that has a corresponding set of X-ray optical gratings is used to carry out the phase contrast measurement exclusively, or at least additionally, while at least one other focus/detector system which is arranged on the gantry with an angular offset and is free from X-ray optical gratings is used exclusively to carry out the absorption measurement.

In an additional and advantageous variant of at least one embodiment, it is also proposed that, when two different focus/detector systems are available-each of the two focus/detector systems is operated with a different accelerating voltage, that is to say with a different energy spectrum. It is possible as a result to obtain additional knowledge relating to the composition of the trans-irradiated matter on the basis of the different energy-dependent absorption relationships. At the same time, it is also possible to operate with different energies not only with reference to the absorption measurement, but also with reference to the measurement of the phase shift. Thus, in the first focus/detector system it is possible to use an anode material that produces a preferred X-ray line in a first energy range, the grating system used being required to be set to this energy, while in the second focus/detector system use is made of another anode material with an X-ray line arranged different in terms of energy, and in this way different, energy-dependent phase shifts can be measured and conclusions can be drawn relating to the composition of the scanned examination object. It may be pointed out in addition that although it is sufficient in principle to measure three values per ray for measuring the phase shift, doing so with an offset analysis grating, in order to determine the phase shift, it can nevertheless be advantageous to carry out a larger number of measurements (at least six measurements would be advantageous), in order to compensate possible errors, produced by quantum noise, for example.

In addition to the above-described method, the inventors also propose a computed tomography system in at least one embodiment for producing tomographic images that has the following features:

at least one focus/detector system that is arranged on a gantry in a fashion rotatable about an examination object is provided, with a set of three trans-irradiated X-ray optical gratings of parallel alignment between focus and detector, by which the phase shift of the radiation during penetration of the examination object can be measured in a ray-wise resolved fashion, in which case a first grating is arranged between the at least one focus and the examination object, a second grating is arranged between the examination object and the detector, a third grating is arranged between the second grating and the detector, an apparatus is provided for displacing the third grating relative to the second grating in a fashion perpendicular to the ray direction and perpendicular to the longitudinal direction of the grating lines, means for reconstructing tomographic absorption images and phase contrast images, and means for superposing and for displaying the superposed tomographic absorption images and phase contrast images.

As already described above, it can be advantageous here to provide the CT system, in at least one embodiment, with at least one further focus/detector system that is arranged with an angular offset on the gantry. This can either be free from X-ray optical gratings and serve exclusively for measuring absorption, or it is also possible to use a further focus/detector system that has a set of X-ray optical gratings that is set to an energy range other than that of the set of X-ray optical gratings of the first focus/detector system. It is to be assumed in this case that the energy range to which the respective grating system is set corresponds to a characteristic line in the energy spectrum of the respective X-ray tubes used and to the anode material thereof.

In accordance with the basic idea of at least one embodiment of the invention, the inventors also propose a focus/detector system having an X-ray apparatus, comprising at least:

- a radiation source with a focus and an opposing planar detector with a multiplicity of detector elements,
- a set of three trans-irradiated X-ray optical gratings of parallel alignment between focus and detector, by which the phase shift of the radiation during penetration of the examination object can be measured in a fashion resolved into rays, in which case
- a first grating is arranged between the at least one focus and the examination object,
- a second grating is arranged between the examination object and the detector,
- a third grating is arranged between the second grating and the detector,
- an apparatus is provided for displacing the third grating relative to the second grating in a fashion perpendicular to the ray direction and perpendicular to the longitudinal direction of the grating lines.

Such an X-ray system need not necessarily be used only to produce computed tomography images; there is also the possibility of using such a system to produce projection images, it being possible in each case to apply the measured phase shift of the respective X-ray as individual pixel value.

Such an X-ray system should also have at least one device, this preferably being an arithmetic logic unit having at least one corresponding computer program and which is designed for calculating the phase shift from a number of intensity measurements of the same ray with the aid, of a differently offset third grating.

It is also possible to provide at least one device, preferably likewise an arithmetic logic unit with an appropriate computer program, that is equipped for calculating the absorption by summing or forming the average of a number of intensity measurements of the same ray with the aid of a differently offset third grating. It is likewise possible to provide at least one device that is suitable for superposing and displaying the superposed absorption images and phase contrast images.

The inventors also claim, furthermore in at least one embodiment, a method for producing projective X-ray images of an examination object, preferably a patient, having an X-ray system, at least the following method steps being carried out:

- the examination object is trans-irradiated by a beam emanating from the focus of an X-ray tube,
- the received radiation intensity is measured with the aid of at least one detector, there being arranged between the at least one X-ray tube and the at least one detector a set of X-ray optical gratings that are trans-irradiated by the X-radiation and enable a phase contrast measurement, and a first grating is arranged between the focus and an examination object, and two gratings are arranged between the examination object and detector,
- for each ray lying in space between the focus and detector and that penetrates the examination object, at least three intensity measurements are determined with the aid of detector-side gratings respectively arranged offset from one another for the phase shift from this ray upon passage through the object,
- phase contrast images whose pixel values represent the phase shift per ray are produced from the measured phase shifts of the rays,
- the absorption of each ray is determined upon passage through the examination object,
- projective absorption images are produced from the absorption measurements, and
- subsequently, the projective absorption images and the projective phase contrast images are superposed and displayed.

Before the superposition of the projective images, the latter can likewise first be subjected to image processing just like the CT images.

Moreover, a weighted superposition of the projective phase contrast images and the projective absorption images can be carried out, in which case it is on the one hand Possible for the viewer or operator to set the weighting manually in accordance with his visual impression, or it is possible to undertake the weighting in accordance with predetermined properties of the images to be superposed, doing so individually, if appropriate differently locally.

In a preferred way, the measurement of the absorption of a ray is also carried out in the case of the projective images by summing up or forming the average of all the measured values with the aid of a differently displaced grating.

It is, furthermore, to be noted that in the case of the above-described focus/detector system, the grating arrangement is to satisfy the following geometric conditions in the case of use both in a CT and in an X-ray system for producing simple projective images:

$$p_1 = 2 \times \frac{p_0 \times p_2}{p_0 + p_2}$$

$$p_0 = p_2 \times \frac{l}{d},$$

$$d = \frac{l \times d^=}{l - d^=},$$

where $$d^= = \frac{1}{2} \times \left(\frac{p_1^2}{4\lambda}\right),$$

$$h_1 = \frac{\lambda}{2(n-1)},$$

in which case:

$p_x$=grating period of the grating $G_x$, l=distance of the source grating $G_0$ from the phase grating, d=distance of the phase grating $G_1$ from the analysis grating $G_2$ in fan beam geometry, d═=distance of the phase grating $G_1$ from the analysis grating $G_2$ in parallel geometry,
λ=wavelength of the radiation yield,
$h_1$=height of the grating $G_1$ in the radiation direction, and
n=refractive index of the grating material.

It may, furthermore, be pointed out that in the practical execution with the gratings used for contrast improvement the gaps between the grating lines can be filled with a highly absorbing material. Gold may be used for this, for example. In principle, at least the source and analysis gratings functioning as absorption gratings should be designed such that they reach a contrast factor of at least $e^{-1}$.

Thus, overall, a method is described in at least one embodiment for producing projective and tomographic images in X-radiation, which method can image structures of similar composition particularly well by combined evaluation of the behavior of the examination object with reference to the phase shift upon passage of the X-radiation and the absorption thereof. Moreover, at least one embodiment of the invention also exhibits an X-ray system and a CT system which is suitable for carrying out this method and is equipped in each case with a source grating, a phase grating and an analysis grating.

BRIEF DESCRIPTION OF THE DRAWINGS

The invention is described in more detail below with reference to the example embodiment and with the aid of the figures, only the features necessary for understanding the invention being illustrated. The following reference symbols are used in this case: 1: CT system; 2: first X-ray tube; 3: first detector; 4: second X-ray tube; 5: second detector; 6: gantry housing; 7: patient; 8: patient couch; 9: system axis; 10: control and arithmetic logic unit; 11: memory; 12: schematic of the inventive method; A: path A; B: path B; $D_1$: detector; d: distance; dN/N: relative photon flux; $E_x$: detector elements; $F_1$: focus; $G_0$: source grating; $G_1$: phase grating; $G_2$: analysis grating; $h_0$, $h_1$, $h_2$: height of the grating webs; I: radiation intensity; $I_{ph}$: phase contrast image; $I_A$: absorption image; $K_\alpha$, $K_\beta$: characteristic X-ray peaks; l: distance; P: patient; $p_0$, $p_1$, $p_2$: period of the grating lines; $Prg_x$: programmes; S: system axis; $S_1$, $S_2$, $S_i$: X-rays; w: extent of the focus; $x_G$: offset of the grating in the x-direction; x, y, z: Cartesian coordinates; φ: phase shift.

In detail:

FIG. 1 shows a 3D schematic of a focus/detector system with grating set for determining phase shifts;

FIG. 2 shows a longitudinal section through a focus/detector system, including an illustration of source grating, phase grating and analysis grating and their grating structure;

FIG. 3 shows a longitudinal section through a focus/detector system of a CT, including phase grating, analysis grating and detector for displaying the interference phenomenon;

FIG. 4 shows the Brems spectrum of a tungsten anode with characteristic lines for different accelerating voltages and the use of a hardening filter;

FIG. 5 shows a flow diagram of an embodiment of the inventive method with the use of an X-ray spectrum;

FIG. 7 shows a flow diagram of an embodiment of the inventive method with the use of different X-ray spectra with the aid of two focus/detector systems.

DETAILED DESCRIPTION OF EXAMPLE EMBODIMENTS

Figure 6:
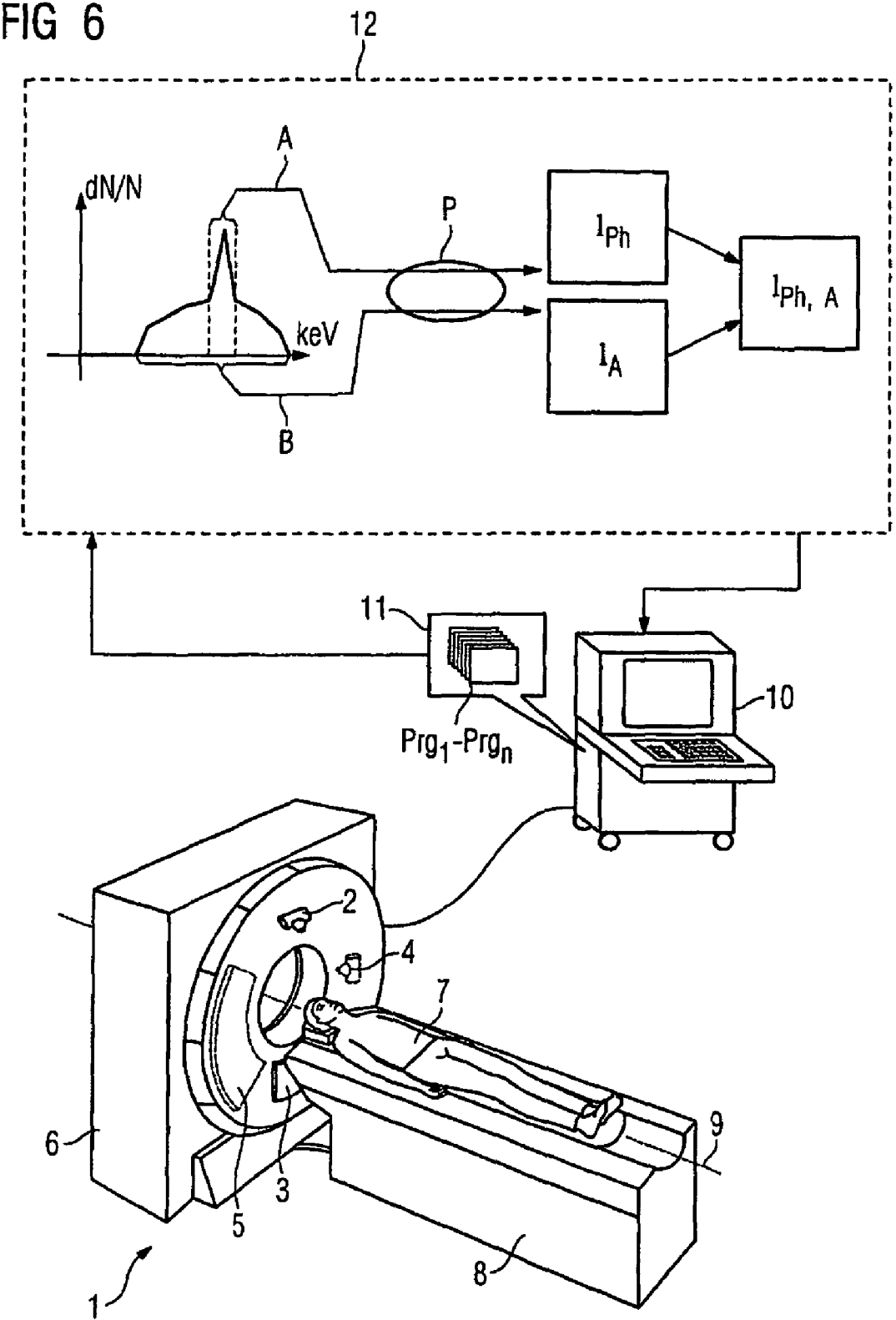
FIG. 6 shows the X-ray CT in a 3D view.

FIG. 1 shows a 3D schematic of a focus/detector system of an X-ray CT having, as examination object, a patient P lying in the beam path. The focus $F_1$ and the detector $D_1$ are arranged on a gantry (not illustrated in more detail here) and move circularly about the system axis S. If a linear movement of the patient P in the direction of the system axis is additionally carried out during the rotation of the focus/detector system, this results in a spiral scanning, known per se, of the patient P. Three X-ray optical gratings $G_0$, $G_1$ and $G_2$ are arranged in the beam path of the focus/detector system, the first grating $G_0$, which is also termed source grating, being fitted in the immediate vicinity of the focus $F_1$ and being trans-irradiated by the X-radiation.

Following thereafter in the propagation direction of the X-radiation is the actual examination object or the patient P. The second grating $G_1$, termed phase grating, firstly follows upstream of the detector $D_1$ lying on the other side of the system axis S. Following thereafter in the direction of radiation is the third grating $G_2$, termed analysis grating, that is advantageously arranged immediately upstream of the detector $D_1$. The detector $D_1$ has at least one row with a multiplicity of detector elements, the detector $D_1$ preferably being designed as a multirow detector that is equipped with a multiplicity of detector rows that are arranged in parallel and each have a multiplicity of detector elements. The connecting lines between the focus $F_1$ and the individual detector elements represent in each case during scanning an X-ray beam that is arranged in space and whose change in intensity is measured by the respective detector element.

It is pointed out that in the case of so-called C-arc units, which also belong to the class of the CT systems mentioned here, the detector $D_1$ is not, as shown, designed as a cylindrical segment about the focus $F_1$, but has a planar shape. In the case of projective X-ray systems which do not move about the examination object during scanning, the detector $D_1$ is generally likewise of planar design.

The line orientation of the gratings $G_0$ to $G_2$ is so regular that the grating lines of all three gratings run parallel to one another. Furthermore, it is advantageous, though not necessary, when the grating lines are oriented parallel or perpendicular to the system axis S, the gratings $G_0$ to $G_2$ mostly being of planar design and being aligned perpendicular to the center line between the focal point and detector midpoint. However, there is also the possibility in principle of adapting the surface of the gratings to the optical path of the light cone such that at each location the gratings are intersected perpendicularly by the ray connection between the focus and the respective detector element, the result being a corresponding curvature of the gratings.

An inventive focus/detector system with a grating set $G_0$ to $G_2$ is illustrated schematically once again in FIG. 2. Located upstream of the first grating $G_0$ is the focus $F_1$, whose greatest extent is denoted by w. The first grating $G_0$ has a period $p_0$ of the grating line and a height $h_0$ of the grating webs. The gratings $G_1$ and $G_2$ are correspondingly also equipped with a height $h_1$ or $h_2$, and a period $p_1$ or $p_2$. The functioning of the inventive method requires that the distance l between the grating $G_0$ and the grating $G_1$, and the distance d between the grating $G_1$ and the grating $G_2$ have a specific ratio to one another. It holds here that $$p_0 = p_2 \times \frac{l}{d}.$$

The distance of the detector $D_1$ with its detector elements $E_1$ to $E_n$ from the last grating $G_2$ is unimportant. The height $h_1$ of the webs of the phase grating should be selected in this case such that the following formula holds in accordance with the wavelengths considered, that is to say the energy considered for the X-radiation, and with reference to the respective grating material:

$$h = \frac{\lambda}{2(n-1)}.$$

Here n denotes the refractive index of the grating material, and λ the wavelengths of the X-ray beams for which the phase shift is to be measured. This grating is, for example, set to an energy that corresponds to a characteristic line in the X-ray spectrum of the anode used. With the currently customary tungsten anodes, it is, for example, possible to use the $K_\alpha$ line. However, it is also possible to use the $K_\beta$ line lying close thereto. When other anode materials are selected, other energies, and thus other dimensions of the phase grating, correspondingly become necessary.

The height $h_2$ of the analysis grating must be sufficient to produce effective absorption differences between the webs trans-irradiated by the X-radiation and the largely free sites of the grating, in order to produce an appropriate Moiré pattern on the rear side.

For the purpose of better understanding, FIG. 3 once again shows the individually coherent radiation that is arriving from the grating $G_0$ and penetrates the patient P, phase shift phenomena coming about after the penetration of the patient P. As a result, when the grating $G_1$ is penetrated there is produced an interference pattern, illustrated by the gray shading, that, with the aid of the grating $G_2$ on the adjoining detector $D_1$ and the detector elements thereof, leads to different radiation intensities per detector element, a so-called Moiré pattern being formed there. If, for example, the detector element $E_i$ is considered as a function of an offset $x_G$ of the analysis grating $G_2$, and if the intensity $I(E_i(x_G))$ is plotted as a function of the offset $x_G$ against the intensity I, the result is a sinusoidal rise and fall of the intensity I at this detector element $E_i$. If these measured radiation intensities I are plotted for each detector element $E_i$ or $E_j$ as a function of the offset $x_G$, it is possible to approximate the function $I(E_i(x_G))$ or $I(E_j(x_G))$ for the various detector elements, which after all form the spatial X-ray beam between the focus and the respective detector element. The phase shift φ relative to one another can be determined for each detector element from the functions. It holds that:

$$\varphi = 2\pi n \frac{v}{\lambda},$$

v corresponding to the size of a voxel or pixel in the examined object, n being the refractive index thereof, and λ representing the wavelength of the X-radiation.

This means that for each ray in space it is possible by means of at least three measurements with an offset analysis grating in each case to determine the phase shift per ray, from which either it is possible in the case of projective X-ray images to calculate the pixel values of a projective image directly or, in the case of a CT examination, projections are prepared whose pixel values correspond to the phase shift, so that it is possible therefrom with the aid of reconstruction methods known per se to calculate which volume element in the examination object is to be ascribed to which part of the measured phase shift. It follows that what is calculated are either sectional images or volume data that reflect the spatial effect of the examined object on the phase shift of an X-radiation. Since even slight differences in composition exert a strong effect on the phase shift, it is possible thereby to reproduce very richly detailed and contrasting volume data of materials that are relatively similar to one another, in particular of soft-part tissue.

If the aim is now additionally also to prepare an absorption image by using the sum of the intensity measurements at the individual detector elements of a detector in order to determine the phase shift, it is possible by summing up the individual measurements for differently offset analysis gratings to average the effect of the analysis grating therefrom, and thus to obtain a direct measure of the absorption values of the respective ray, that is to say it is possible on the basis of the measured data for the phase shift also to calculate a data record that reproduces an absorption value for each ray such that these absorption values can, in a way known per se, either be converted to direct projection absorption images or, with the aid of known reconstructions, be converted into tomographic absorption images.

Since the above-described method for determining the phase shift of X-ray beams traversing an object is very energy-selective, the phase grating should be set with reference to its dimensions to energy ranges of the radiation used in which there is a photon number that is as high as possible.

If, for example, a tungsten anode is being used, energy spectra result as a function of the accelerating voltage, as is illustrated in FIG. 4. Here, a strong respective peak is shown on the left and right in the energy spectra; it represents the characteristic radiation of the tungsten material used here. The $K_\alpha$ line of the tungsten is shown on the left, and the $K_\beta$ line on the right. It is particularly advantageous according to the invention when the phase grating is oriented exactly with one such characteristic line with reference to its web height $h_1$.

FIG. 5 shows, once again, in a schematic flow diagram, how the phase contrast measurement is carried out with the aid of an energy spectrum (represented on the left) that has a characteristic X-ray line, this being done in a first path A by using this characteristic line and the large number of photons occurring there in this region, and by using this characteristic radiation, while the absorption measurement is carried out in the lower path by using the entire radiation energy region in path B. Projective or tomographic phase contrast images $I_{Ph}$ are determined via the path A, and projective or tomographic absorption images $I_A$ are determined via the path B, said images subsequently being used by superposition to form image data $I_{Ph,A}$ that respectively contain informative image information from the two regions.

A complete computer CT system for carrying out an embodiment of the inventive method is demonstrated in FIG. 6. This shows the CT system 1, which has a first focus/detector system with an X-ray tube 2 and opposing detector 3, which are arranged on a gantry (not illustrated in greater detail) in a gantry housing 6. A grating system in accordance with FIGS. 1 to 3 is arranged in the beam path of the first focus/detector system 2, 3, such that the patient 7, who is located on a patient couch 8 that can be displaced along the system axis 9, can be pushed into the beam path of the first focus/detector system and scanned there. The control of the CT system is carried out by means of an arithmetic logic and control unit 10 in which there are stored in a memory 11 programs $Prg_1$ to $Prg_n$ that carry out the previously described inventive methods, and reconstruct corresponding tomographic images from the measured ray-dependent phase shifts and absorptions. The carrying out of embodiments of these inventive methods is indicated, in accordance with FIG. 5, in the box 12 illustrated with dashes.

Instead of the single focus/detector system, a second focus/detector system can optionally be arranged in the gantry housing. This is illustrated in FIG. 6 by the X-ray tube 4 shown with dashes, and by the detector 5 illustrated by dashes.

If such a CT system with two focus/detector systems is used, a method such as is illustrated in FIG. 7 can, for example, be carried out. The situation of the two focus/detector systems is described by the paths I and II. By way of example, the two detector systems use here the same anode material, specifically tungsten, the set of X-ray optical gratings being adapted in the first detector system I to the $K_\alpha$ line of tungsten, such that here the phase shift of X-radiation is measured in this energy region, and a phase contrast image $I_{Ph(EI)}$ is produced, via the path $A_I$. At the same time, an absorption image $I_{A(EI)}$ is produced by summing up over the various measurements for determining the phase contrast in path $B_I$. It is to be noticed here that in this case "image" is understood to mean tomographic image data that, of course, represent the entire scanned volume.

In accordance with the other energy adaptation of the set of X-ray optical gratings in the second focus/detector system II and the energy spectrums differing there, the phase shift of the X-radiation with energies of the $K_\beta$ line of tungsten is detected there, and a corresponding phase contrast image $I_{Ph(EII)}$ is produced, and at the same time an absorption image $I_{A(EII)}$ is also produced here via the second path $B_{II}$.

Subsequently, the phase contrast image data and the absorption image data obtained in this way can be processed and mixed taking account of appropriate weightings, such, that a very richly detailed image data record $I_{Ph(EI, EII), A(EI, EII)}$ results.

It also remains to be noted here that, in the last-named example of an embodiment of the inventive method, other combinations of different or identical accelerating voltage are also possible, as is adaptation of the gratings to different or identical characteristic radiation energies.

It goes without saying that the above-named features of embodiments of the invention can be used not only in the combination respectively specified, but also in other combinations or on their own, without departing from the scope of the invention.

Overall, it has thus been shown by embodiments of the invention that it is possible by measuring the phase shift of X-radiation to produce both projective and tomographic displays of an examination object which in the case of a similar tissue display structural differences in a clearly structural fashion and that, in particular, such images can show structures in particularly rich detail by using the phase contrast and absorption methods.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A method for producing tomographic images of an examination object, using an X-ray CT system, the method comprising:
scanning the examination object at least one of circularly and spirally with the aid of at least one X-ray tube having a focus;
measuring received radiation intensity with the aid of at least one detector, there being arranged, between the at least one X-ray tube and the at least one detector, a set of X-ray optical gratings that are trans-irradiated by the X-radiation and enable a phase contrast measurement, a first grating being arranged between the focus and an examination object, and two gratings being arranged between the examination object and detector;
determining, for each ray lying in space between the focus and detector and that penetrates the examination object, at least three intensity measurements with the aid of detector-side gratings respectively arranged offset from one another for the phase shift from this ray upon passage through the object;
reconstructing tomographic phase contrast images from the measured phase shifts of the rays;
determining the absorption of each ray upon passage through the examination object;
reconstructing tomographic absorption images from the absorption measurements; and
subsequently superposing and displaying the tomographic absorption images and the tomographic phase contrast images.

2. The method as claimed in claim 1, wherein at least one of the tomographic phase contrast images and the tomographic absorption images are subjected to image processing before superposition.

3. The method as claimed in claim 2, wherein a weighted superposition of the tomographic phase contrast images and the tomographic absorption images is carried out.

4. The method as claimed in claim 1, wherein a weighted superposition of the tomographic phase contrast images and the tomographic absorption images is carried out.

5. The method as claimed in claim 4, wherein the weighting of the two images is settable by the viewer.

6. The method as claimed in claim 4, wherein the weighting of the two images is undertaken at different locations.

7. The method as claimed in claim 1, wherein the measurement of the absorption of a ray is carried out by at least one of summing up and forming the average of all the measured values with the aid of a differently displaced grating.

8. The method as claimed in claim 1, wherein a phase contrast measurement with the aid of at least a first focus/detector system having trans-irradiated X-ray optical gratings, and at least one absorption measurement is carried out by at least a second focus/detector system, arranged with an angular offset, without an X-ray optical grating.

9. The method as claimed in claim 7, wherein the X-ray tubes of the at least two focus/detector systems are operated with a different accelerating voltage.

10. The method as claimed in claim 1, wherein the grating geometry of at least one focus/detector system is tuned to a characteristic X-ray line of the anode material.

11. The method as claimed in claim 1, wherein, depending on the ray and focus/detector system, at least six measurements are carried out with a different grating offset in order to determine the phase shift.

12. A CT system for producing tomographic images, comprising:
at least one focus/detector system, arranged on a gantry in a fashion rotatable about an examination object, including a set of three trans-irradiated X-ray optical gratings of parallel alignment between focus and detector, by which the phase shift of the radiation during penetration of the examination object is measurable in a ray-wise resolved fashion, a first grating being arranged between the at least one focus and the examination object, a second grating being arranged between the examination object and the detector and a third grating being arranged between the second grating and the detector, the at least one focus/detector system further including an apparatus for displacing the third grating relative to the second grating in a fashion perpendicular to the ray direction and perpendicular to the longitudinal direction of the grating lines, means for reconstructing tomographic absorption images and phase contrast images; and means for superposing the tomographic absorption images and phase contrast images, and for displaying the superposed images.

13. The CT system as claimed in claim 12, wherein there is arranged, on the gantry with an angular offset, at least one further focus/detector system that is free from X-ray optical gratings and serves exclusively for measuring absorption.

14. The CT system as claimed in claim 13, wherein the grating arrangement satisfies the following geometric conditions:

$$p_1 = 2 \times \frac{p_0 \times p_2}{p_0 + p_2}$$

$$p_0 = p_2 \times \frac{l}{d},$$

$$d = \frac{l \times d^=}{l - d^=},$$

where $$d^= = \frac{1}{2} \times \left(\frac{p_1^2}{4\lambda}\right),$$

$$h_1 = \frac{\lambda}{2(n-1)},$$

wherein:

$P_x$=grating period of the grating $G_x$, l=distance of the source grating $G_0$ from the phase grating, d=distance of the phase grating $G_1$ from the analysis grating $G_2$ in fan beam geometry, $d^=$=distance of the phase grating $G_1$ from the analysis grating $G_2$ in parallel geometry, $\lambda$=wavelength of the radiation yield, $h_1$=height of the grating $G_1$ in the radiation direction, and n=refractive index of the grating material.

15. The CT system as claimed in claim 12, further comprising an arithmetic logic and control unit.

16. The CT system as claimed in claim 12, wherein the grating arrangement satisfies the following geometric conditions:

$$p_1 = 2 \times \frac{p_0 \times p_2}{p_0 + p_2}$$

$$p_0 = p_2 \times \frac{l}{d},$$

$$d = \frac{l \times d^=}{l - d^=},$$

where $$d^= = \frac{1}{2} \times \left(\frac{p_1^2}{4\lambda}\right),$$

$$h_1 = \frac{\lambda}{2(n-1)},$$

wherein:

$p_x$=grating period of the grating $G_x$, l=distance of the source grating $G_0$ from the phase grating, d=distance of the phase grating $G_1$ from the analysis grating $G_2$ in fan beam geometry, $d^=$=distance of the phase grating $G_1$ from the analysis grating $G_2$ in parallel geometry, $\lambda$=wavelength of the radiation yield, $h_1$=height of the grating $G_1$ in the radiation direction, and n=refractive index of the grating material.

17. A non-transitory computer readable storage medium of or for a CT system, wherein the storage medium contains a program code to perform the method of claim 1 when executed during operation of the CT system.

18. A focus/detector system of an X-ray apparatus, comprising:

a radiation source with a focus and an opposing planar detector with a multiplicity of detector elements; and a set of three trans-irradiated X-ray optical gratings of parallel alignment between focus and detector, by which the phase shift of the radiation during penetration of the examination object is measurable in a fashion resolved into rays, a first grating being arranged between the at least one focus and the examination object, a second grating being arranged between the examination object and the detector, a third grating being arranged between the second grating and the detector, and an apparatus being provided for displacing the third grating relative to the second grating in a fashion perpendicular to the ray direction and perpendicular to the longitudinal direction of the grating lines.

19. The focus/detector system as claimed in claim 18, wherein the grating arrangement satisfies the following geometric conditions:

$$p_1 = 2 \times \frac{p_0 \times p_2}{p_0 + p_2}$$

$$p_0 = p_2 \times \frac{l}{d},$$

$$d = \frac{l \times d^=}{l - d^=},$$

where $$d^= = \frac{1}{2} \times \left(\frac{p_1^2}{4\lambda}\right),$$

$$h_1 = \frac{\lambda}{2(n-1)},$$

wherein:

$P_x$=grating period of the grating $G_x$, l=distance of the source grating $G_0$ from the phase grating, d=distance of the phase grating $G_1$ from the analysis grating $G_2$ in fan beam geometry, $d^=$=distance of the phase grating $G_1$ from the analysis grating $G_2$ in parallel geometry, $\lambda$=wavelength of the radiation yield, $h_1$=height of the grating $G_1$ in the radiation direction, and n=refractive index of the grating material.

20. An X-ray system comprising at least one focus/detector system as claimed in claim 19.

21. An X-ray system comprising at least one focus/detector system as claimed in claim 18.

22. The X-ray system as claimed in claim 21, further comprising means for calculating the phase shift from a number of intensity measurements of the same ray with the aid of a differently offset third grating.

23. The X-ray system as claimed in claim 22, further comprising means for calculating the absorption by summing or forming the average of a number of intensity measurements of the same ray with the aid of a differently offset third grating.

24. The X-ray system as claimed in claim 23, further comprising means for superposing and displaying the superposed absorption images and phase contrast images.

25. A method for producing projective X-ray images of an examination object having an X-ray system, the method comprising:
  trans-irradiating the examination object by a beam emanating from the focus of an X-ray tube,
  measuring the received radiation intensity with the aid of at least one detector, there being arranged between the at least one X-ray tube and the at least one detector a set of X-ray optical gratings that are trans-irradiated by the X-radiation and enable a phase contrast measurement, and a first grating being arranged between the focus and an examination object and two gratings being arranged between the examination object and detector;
  determining, for each ray lying in space between the focus and detector and that penetrates the examination object, at least three intensity measurements with the aid of detector-side gratings respectively arranged offset from one another for the phase shift from the respective ray upon passage through the object;
  producing phase contrast images, whose pixel values represent the phase shift per ray, from the measured phase shifts of the rays;
  determining the absorption of each ray upon passage through the examination object;
  producing projective absorption images from the absorption measurements; and
  subsequently superposing and displaying the projective absorption images and the projective phase contrast images.

26. The method as claimed in claim 25, wherein at least one of the projective phase contrast images and the projective absorption images are subjected to image processing before superposition.

27. The method as claimed in claim 25, wherein a weighted superposition of the projective phase contrast images and the projective absorption images is carried out.

28. The method as claimed in claim 27, wherein the weighting of the superposed images is settable by the viewer.

29. The method as claimed in claim 28, wherein the weighting of the superposed images is undertaken at different locations.

30. The method as claimed in claim 25, wherein the measurement of the absorption of a ray is carried out by summing up or forming the average of all the measured values with the aid of a differently displaced grating.

* * * * *